US008673350B2

(12) United States Patent
McAllister et al.

(10) Patent No.: US 8,673,350 B2
(45) Date of Patent: Mar. 18, 2014

(54) PHARMACEUTICAL FORMULATIONS

(75) Inventors: Stephen Mark McAllister, Harlow (GB); Ronald K. Raby, Jr., Collegeville, PA (US); Adrian Brown, Harlow (GB)

(73) Assignee: Capsugel Belgium NV, Bornem (BE)

(*) Notice: Subject to any disclaimer, the term of this patent is extended or adjusted under 35 U.S.C. 154(b) by 1382 days.

(21) Appl. No.: 10/565,462

(22) PCT Filed: Jul. 21, 2004

(86) PCT No.: PCT/US2004/023542
§ 371 (c)(1),
(2), (4) Date: Jan. 20, 2006

(87) PCT Pub. No.: WO2005/009830
PCT Pub. Date: Feb. 3, 2005

(65) Prior Publication Data
US 2006/0177496 A1  Aug. 10, 2006

Related U.S. Application Data

(60) Provisional application No. 60/489,159, filed on Jul. 21, 2003.

(51) Int. Cl.
A61K 9/48 (2006.01)
A61K 9/52 (2006.01)
A61K 9/62 (2006.01)
A61K 9/66 (2006.01)

(52) U.S. Cl.
USPC ............ 424/451; 424/455; 424/457; 424/461

(58) Field of Classification Search
None
See application file for complete search history.

(56) References Cited

U.S. PATENT DOCUMENTS

| | | |
|---|---|---|
| 3,186,910 A | 6/1965 | Glassman |
| 3,228,789 A | 1/1966 | Glassman |
| 3,314,809 A | 4/1967 | Klug et al. |
| 3,394,983 A | 7/1968 | Greif et al. |
| 3,399,803 A | 9/1968 | Oglevee et al. |
| 3,723,312 A | 3/1973 | Hay, Jr. |
| 3,779,942 A | 12/1973 | Bolles |
| 4,196,565 A | 4/1980 | Bodenmann et al. |
| 4,250,097 A | 2/1981 | Pfister |
| 4,281,763 A | 8/1981 | Pace |
| 4,417,591 A | 11/1983 | Culver |
| 4,483,846 A | 11/1984 | Koide et al. ............ 424/19 |
| 4,487,327 A | 12/1984 | Grayson |
| 4,498,080 A | 2/1985 | Culver |
| 4,543,138 A | 9/1985 | Bollinger et al. |
| 4,550,238 A | 10/1985 | Van Herle et al. |
| 4,557,180 A | 12/1985 | Glomeau |
| 4,564,363 A | 1/1986 | Bagnall et al. |
| 4,576,284 A | 3/1986 | Wittwer |
| 4,591,475 A | 5/1986 | Tomka et al. |
| D285,837 S | 9/1986 | Wittwer |
| 4,625,513 A | 12/1986 | Glomeau |
| 4,655,840 A | 4/1987 | Wittwer et al. |
| 4,673,438 A | 6/1987 | Wittwer et al. |
| 4,678,516 A | 7/1987 | Alderman et al. |
| 4,696,163 A | 9/1987 | Glomeau |
| 4,705,695 A | 11/1987 | Lehmann et al. |
| 4,724,019 A | 2/1988 | Brown et al. |
| 4,737,357 A | 4/1988 | Lehmann et al. |
| 4,738,724 A | 4/1988 | Wittwer et al. |
| 4,738,817 A | 4/1988 | Wittwer et al. |
| 4,764,378 A | 8/1988 | Keith et al. |
| 4,766,728 A | 8/1988 | Glomeau |
| 4,790,881 A | 12/1988 | Wittwer et al. |
| 4,792,451 A | 12/1988 | Kim |
| 4,793,493 A | 12/1988 | Makiej et al. |
| 4,795,644 A | 1/1989 | Zentner |
| 4,801,460 A | 1/1989 | Goertz et al. |
| 4,806,337 A | 2/1989 | Snipes et al. |
| 4,892,741 A | 1/1990 | Ohm et al. ............ 424/479 |
| 4,899,516 A | 2/1990 | Krieger et al. |
| 4,928,840 A | 5/1990 | Barshay et al. |
| 4,936,461 A | 6/1990 | Makiej et al. |
| 4,964,262 A | 10/1990 | Moser et al. |
| 5,004,601 A | 4/1991 | Snipes |
| 5,074,426 A | 12/1991 | Goodhart et al. |
| 5,082,655 A | 1/1992 | Snipes et al. |
| 5,085,033 A | 2/1992 | Graham |
| 5,110,877 A | 5/1992 | Hoess et al. |

(Continued)

FOREIGN PATENT DOCUMENTS

CA  2211671  2/1996
CA  2253695  11/1998

(Continued)

OTHER PUBLICATIONS

Cuff et al., Pharmaceutical Technology, Jun. 1998, pp. 96-106.
Hu et al., "Characterization of Norfloxacine Release from Tablet Coasted with a New pH Sensitive Polymer, P-4135F", Journal of Drug Targeting, 1999, vol. 7, No. 3, pp. 223-232.
Fukui et al., Int. J. Pharm vol. 217, 2001, pp. 33-43.
Kohri et al., Int. J. Pharm 49(3): 213-221 (1989).
Meyuys et al., Euro J. Pharm. Sci., vol. 24, 2005, pp. 207-212.
Nakamichi et al., J. Drug Delivery Sci & Tech. vol. 14, No. 3, pp. 193-198, 2004.
U.S. Appl. No. 12/689,015, Clark et al.
U.S. Appl. No. 12/741,596, Brown et al.

(Continued)

Primary Examiner — Susan Tran
(74) Attorney, Agent, or Firm — Finnegan, Henderson, Farabow, Garrett & Dunner LLP

(57) ABSTRACT

The present invention is directed to novel pharmaceutically acceptable polymeric compositions suitable for injection molding of single or multi-component pharmaceutical dosage forms comprising a plurality of drug substance containing sub-units, being capsule compartments and/or solid sub-units comprising a solid matrix of a polymer which contains a drug substance, the sub-units being connected together in the assembled dosage form by a weld between parts of the assembled dosage form.

26 Claims, No Drawings

(56) References Cited

U.S. PATENT DOCUMENTS

| | | |
|---|---|---|
| 5,135,752 A | 8/1992 | Snipes |
| 5,139,790 A | 8/1992 | Snipes |
| 5,155,172 A | 10/1992 | Siol et al. |
| 5,219,931 A | 6/1993 | Siol et al. |
| 5,225,202 A | 7/1993 | Hodges et al. |
| 5,236,689 A | 8/1993 | Wong et al. |
| RE34,390 E | 9/1993 | Culver |
| 5,244,668 A | 9/1993 | Snipes |
| 5,270,397 A | 12/1993 | Rhein et al. |
| 5,312,008 A | 5/1994 | Davis |
| 5,312,388 A | 5/1994 | Wong et al. |
| 5,387,421 A | 2/1995 | Amidon et al. |
| 5,443,461 A | 8/1995 | Atkinson et al. |
| 5,456,919 A | 10/1995 | Patell et al. |
| 5,489,436 A | 2/1996 | Hoy et al. |
| 5,548,033 A | 8/1996 | Vetter et al. |
| 5,552,159 A | 9/1996 | Mueller et al. |
| 5,644,011 A | 7/1997 | Lehmann et al. |
| 5,652,316 A | 7/1997 | May et al. |
| 5,672,359 A | 9/1997 | Digenis et al. |
| 5,674,530 A | 10/1997 | Crison et al. |
| 5,705,189 A | 1/1998 | Lehmann et al. |
| 5,741,519 A | 4/1998 | Rosenberg et al. |
| 5,750,143 A | 5/1998 | Rashid et al. |
| 5,769,267 A | 6/1998 | Duynslager et al. |
| 5,770,224 A | 6/1998 | Rashid et al. |
| 5,861,173 A * | 1/1999 | Nishioka et al. ............... 424/480 |
| 5,939,099 A | 8/1999 | Grabowski et al. |
| 5,976,571 A | 11/1999 | Crison et al. |
| 6,063,821 A | 5/2000 | Breitenbach et al. |
| 6,139,875 A | 10/2000 | Adams et al. |
| 6,153,218 A | 11/2000 | Barnwell et al. |
| 6,200,600 B1 | 3/2001 | Rashid |
| 6,207,191 B1 | 3/2001 | Crison et al. |
| 6,248,807 B1 | 6/2001 | Sosa et al. |
| 6,270,797 B1 * | 8/2001 | Gidwani et al. ............... 424/457 |
| 6,284,803 B1 | 9/2001 | Kothrade et al. |
| 6,287,470 B1 | 9/2001 | Vetter et al. |
| 6,290,990 B1 | 9/2001 | Grabowski et al. |
| 6,309,666 B1 | 10/2001 | Hatano et al. |
| 6,318,650 B1 | 11/2001 | Breitenbach et al. |
| 6,322,816 B1 | 11/2001 | Zeidler et al. |
| 6,367,228 B1 | 4/2002 | Wurst et al. |
| 6,368,629 B1 | 4/2002 | Watanabe et al. |
| 6,387,401 B2 | 5/2002 | Rosenberg et al. |
| 6,528,089 B1 | 3/2003 | Kothrade et al. |
| 6,548,513 B1 | 4/2003 | Creekmore et al. |
| 6,551,617 B1 | 4/2003 | Corbo et al. |
| D481,456 S | 10/2003 | McAllister et al. |
| D493,518 S | 7/2004 | McAllister et al. |
| 6,765,046 B1 | 7/2004 | Numrich et al. |
| D501,549 S | 2/2005 | McAllister et al. |
| D501,550 S | 2/2005 | McAllister et al. |
| D506,545 S | 6/2005 | McAllister et al. |
| D516,714 S | 3/2006 | McAllister et al. |
| 7,014,810 B2 | 3/2006 | Krull et al. |
| 7,163,693 B1 | 1/2007 | Clarke et al. |
| 7,217,381 B2 | 5/2007 | Sowden |
| 7,476,403 B2 * | 1/2009 | Li et al. ............... 424/489 |
| 2001/0008637 A1 | 7/2001 | Hochrainer et al. |
| 2003/0029558 A1 | 2/2003 | Hochrainer et al. |
| 2003/0049311 A1 * | 3/2003 | McAllister et al. ............... 424/452 |
| 2003/0068369 A1 | 4/2003 | McAllister et al. |
| 2003/0194428 A1 | 10/2003 | Miller et al. |
| 2003/0194429 A1 | 10/2003 | Miller et al. |
| 2003/0194430 A1 | 10/2003 | Miller et al. |
| 2004/0115256 A1 | 6/2004 | MacAllister et al. |
| 2004/0131668 A1 | 7/2004 | Hochrainer et al. |
| 2004/0166080 A1 | 8/2004 | Assmus et al. |
| 2004/0166153 A1 | 8/2004 | McAllister et al. |
| 2005/0267250 A1 | 12/2005 | Theil et al. |
| 2006/0121248 A1 | 6/2006 | Lorenz et al. |
| 2007/0055017 A1 | 3/2007 | Schultes et al. |
| 2007/0066708 A1 | 3/2007 | Goldacker et al. |
| 2007/0112135 A1 | 5/2007 | Wicker et al. |
| 2007/0178156 A1 | 8/2007 | Brown et al. |
| 2007/0222117 A1 | 9/2007 | Hoess et al. |
| 2007/0276093 A1 | 11/2007 | Schultes et al. |
| 2010/0074947 A1 | 3/2010 | Brown et al. |

FOREIGN PATENT DOCUMENTS

| | | |
|---|---|---|
| CA | 2253700 | 11/1998 |
| CA | 2257547 | 7/1999 |
| EP | 0091908 | 4/1983 |
| EP | 0086093 | 8/1983 |
| EP | 141397 | 10/1984 |
| EP | 0211079 | 1/1985 |
| EP | 143524 | 6/1985 |
| EP | 0228067 | 12/1986 |
| EP | 349103 B1 | 1/1990 |
| EP | 0364060 | 4/1990 |
| EP | 717986 B1 | 6/1996 |
| EP | 0 759 303 | 2/1997 |
| EP | 0776660 | 6/1997 |
| GB | 2187703 | 0/1987 |
| GB | 1496737 | 6/1975 |
| GB | 2172569 | 3/1985 |
| JP | 2003-171277 A | 6/2003 |
| WO | WO 90/12567 | 11/1990 |
| WO | WO 92/13521 | 8/1992 |
| WO | WO 94/09743 | 5/1994 |
| WO | WO 95/13056 | 5/1995 |
| WO | WO 95/16438 | 6/1995 |
| WO | 96/24337 | 8/1996 |
| WO | 97/37642 | 10/1997 |
| WO | 98/30209 | 7/1998 |
| WO | WO 99/27909 | 6/1999 |
| WO | 00/16742 | 3/2000 |
| WO | 00/45793 | 8/2000 |
| WO | WO 01/08666 | 2/2001 |
| WO | WO 01/39751 | 6/2001 |
| WO | WO 01/43935 | 6/2001 |
| WO | WO 02060384 A2 * | 8/2002 |
| WO | WO 02/098625 | 12/2002 |
| WO | WO 03/043601 | 5/2003 |

\* cited by examiner

PHARMACEUTICAL FORMULATIONS

This application is the §371 national stage entry of PCT/US2004/023542, filed 21 Jul. 2004 and claims the benefit of U.S. Provisional Application No. 60/489,159 filed 21 Jul. 2003.

FIELD OF THE INVENTION

This invention relates to the preparation of an injection molded single or multi-component dosage form using novel pharmaceutically acceptable polymeric blends.

BACKGROUND OF THE INVENTION

Various types of pharmaceutical dosage forms are known for oral dosing. Pharmaceutical capsules are well known, generally being intended for oral dosing. Such capsules generally comprise an envelope wall of a pharmaceutically acceptable, e.g. orally ingestible, polymer material such as gelatin, although other materials for capsule walls, e.g. starch and cellulose based polymers are also known. Such capsules generally have soft walls made by making a film on a capsule former, which is then allowed to dry. Rigid walled capsules made by injection molding are also known, see for example U.S. Pat. Nos. 4,576,284; 4,591,475; 4,655,840; 4,738,724; 4,738,817 and 4,790,881 (all to Warner Lambert). These disclose specific constructions of capsules made of gelatin, starch and other polymers, and methods of making them by injection molding of hydrophilic polymer—water mixtures. U.S. Pat. No. 4,576,284 specifically discloses such capsules provided with a cap which closes the capsule, and which is formed in situ on the filled capsule by molding. U.S. Pat. No. 4,738,724 discloses a wide range of rigid capsule shapes and parts.

Multi-compartment capsules, including those of the type where each compartment has different drug release characteristics, or for example, contains a different drug substance or formulation are also known, for example in U.S. Pat. No. 4,738,724 (Warner-Lambert); U.S. Pat. No. 5,672,359 (University of Kentucky); U.S. Pat. No. 5,443,461 (Alza Corp.); WO 95/16438 (Cortecs Ltd.); WO 90/12567 (Helminthology Inst.); DE-A-3727894, and BE 900950 (Warner Lambert); FR 2524311, and NL 7610038 (Tapanhony NV); FR 1,454, 013 (Pluripharm); U.S. Pat. No. 3,228,789 (Glassman); and U.S. Pat. No. 3,186,910 (Glassman) among others. U.S. Pat. No. 4,738,817 discloses a multicompartment capsule with a similar construction to those of U.S. Pat. Nos. 3,228,789 and 3,186,910, made of a water-plasticized gelatin. U.S. Pat. No. 4,738,817 ('817) Witter et al., U.S. Pat. No. 4,790, 881 ('881), Wittwer et al., and EP 0 092 908, Wittwer, F., all discloses injection molded capsules prepared with gelatin and other excipients. Wittwer et al. '817 and '881 also prepare capsules with other hydrophilic polymers, such as hydroxypropylmethyl-cellulose phthalate (HPMCP), methylcellulose, microcrystalline cellulose, polyethylene glycol, cellulose acetate phthalate (CAP) and with polyvinylpyrrolidone. Both U.S. Pat. No. 4,790,881 and EP 0 091 908 propose other polymers having enteric properties suitable for use, including generally acrylates and methacrylates (Eudragits) although none are demonstrated and no specific details are provided.

Pharmaceutical dosage forms are also known which comprise a matrix of a solid polymer, in which a drug substance is dispersed, embedded or dissolved as a solid solution. Such matrixes may be formed by an injection molding process. This technology is discussed in Cuff G, and Raouf F, Pharmaceutical Technology, June (1998) pages 96-106. Some specific formulations for such dosage forms are disclosed in U.S. Pat. Nos. 4,678,516; 4,806,337; 4,764,378; 5,004,601; 5,135,752; 5,244,668; 5,139,790; 5,082,655; 5,552,159; 5,939,099; 5,741,519; 4,801,460; 6,063,821; WO 99/27909; CA 2,227,272; CA 2,188,185; CA 2,211,671; CA 2,311,308; CA 2,298,659; CA 2,264,287; CA 2,253,695; CA 2,253,700; and CA 2,257,547 among others.

U.S. Pat. No. 5,705,189, is directed to a group of co-polymers of methacrylic acid, methyl methacrylate and methyl acrylate, for use as thermoplastic agents in the production of drugs coatings, and capsules. No information is presented on the quality of the capsule formation with respect to warping or other distortions produced by the injection molding process. Nor is shear rate data presented for the viscosity/temperature figures of the emulsions presented therein.

It would also be desirable to prepare a pharmaceutical dosage form in which a pharmaceutically acceptable polymeric blend is extruded by hot melt, or injection molded into a suitable dosage form, which may be multicompartmental, such as a capsule. This pharmaceutical polymeric composition as the dosage form, may provide differing physio-chemical characteristics for each segment containing an active agent, such that a convenient dosage form can be optioned which may include a rapid dissolve, immediate, delayed, pulsatile, or modified release which can be produced by simply selecting the appropriate polymer(s) to be molded for each section.

SUMMARY OF THE INVENTION

The present invention provides for novel pharmaceutical compositions, and their use in making injection molded capsule shells, linkers, spacers, multicomponent injection molded capsule shells, linkers or spacers, multicomponent pharmaceutical dosage forms, and other aspects as defined in the claims and description of this application.

Another embodiment of the invention is to provide an alternative and improved pharmaceutical dosage form which provides, inter alia, greater flexibility in the dosage form adapted to a patient's specific administration requirement, using the novel formulations, or compositions, of pharmaceutically acceptable polymers and suitable excipients in said dosage forms.

Another embodiment of the invention is to provide a process of producing the multicomponent dosage forms comprising the novel pharmaceutically acceptable polymeric blends by injection molding. These multi-component dosage forms are suitable for containing a pharmaceutically acceptable active agent, or agents, for release thereby.

In accordance with the invention, an injection molded capsule shell, and/or linker is provided for with a composition including Eudragit® 4135F.

The capsule shell or linker comprises a solid matrix, and composed of Eudragit® 4135F present in an amount of about 20 to 70% w/w, and a hydroxypropyl cellulose derivative, or blend of hydroxypropylcellulose derivatives, present from about 20 to about 70% w/w. The composition may optionally further comprises dissolution-modifying excipients present in an amount of about 0% w/w to about 30% w/w; a lubricant present in an amount up to about 30% w/w; a plasticizer present in an amount up to about 10% w/w, and a processing agent present in an amount up to about 10% w/w.

In an alternative embodiment, the pharmaceutical dosage form comprises a plurality of sub-units, each being a drug substance-containing capsule compartment. In this case, each compartment is physically separated from at least one adjacent compartment, preferably by a wall made of a pharmaceutically acceptable polymer material. In the case in which at least one of the sub-units is a drug substance-containing capsule compartments its wall thickness is preferably in the range of about 0.3-0.8 mm.

The multi-component dosage form of the invention affords a high degree of versatility in that it can be composed of various combinations of different dosage forms having different release characteristics. For example, the sub-units can be a substantially immediate release sub-unit, a sustained release sub-unit, or a pulsed release sub-unit.

Other objects and advantages of the invention will be apparent from the following description.

DETAILED DESCRIPTION OF THE INVENTION

The present invention is directed to novel compositions of a pharmaceutically acceptable polymer and excipients, which polymeric composition may be injection molded into one or more components which can optionally be utilized together, such as in a stacked or multi-component dosage form. It is recognized that the polymeric blends may be injection molded into a single component that may also contain the active agent for oral administration.

The present invention also relates to the application of a pharmaceutically acceptable film coating over a component comprising the novel pharmaceutically acceptable polymeric blends as described herein. The film coating may be a delayed release formulation, or a pH control formulation as are well known in the art. One suitable coating is Eudragit® L30D-55. The enteric coatings may be applied using standard equipment such as a GMP Aerocoater column coater. The component weight gain is nominally from about 3% to about 5% w/w.

The pharmaceutically acceptable polymeric blends herein are designed to provide consistent, and rapid dissolution profile.

A preferred multicomponent dosage form is that disclosed in WO 01/08666 on Feb. 8, 2001, the contents of which are incorporated by reference herein in its entirety.

The parts of the dosage form of this invention, e.g. a capsule compartment wall, a solid sub-unit, or a closure or linker, comprise a pharmaceutically acceptable polymeric blend (and adhesive material if adhesive welds are formed) which is generally regarded as safe, e.g. for oral ingestion and is capable of being formed into the required shape of a capsule compartment wall, a solid sub-unit, or a closure or linker as described above. A preferred method of forming the polymer material into the desired shape is injection molding, which may be a hot or cold runner injection molding process. Suitable injection molding machines for such a process are known.

The pharmaceutical dosage form may comprises a plurality of capsule compartments each bounded and physically separated from at least one adjacent compartment by a wall made of a pharmaceutically acceptable polymer material, such as described herein, adjacent compartments being connected together in the assembled dosage form, and being retained together by the connection at least prior to administration to a patient, one or more of the compartments containing a drug substance. Suitably in the assembled dosage form of this first embodiment there are at least two, for example three, such capsule compartments. Three or more such compartments may be linearly disposed in the assembled dosage form, e.g. in an arrangement comprising two end compartments at opposite ends of the line, and one or more intermediate compartments. Suitably there may be two such capsule compartments. Suitably one of such two capsule compartments may be made of a material which is a sustained release component, i.e. so that the capsule compartment wall dissolves, bursts or is otherwise breached to release its contents after a time delay, e.g. when the compartment has reached the intestine. Suitably the other of such two capsule compartments may be made of a material which is an immediate release component, i.e. so that the capsule compartment wall dissolves, bursts or is otherwise breached to release its contents immediately or effectively immediately, e.g. when the compartment is in the mouth or stomach.

One or more, e.g. all, of the capsule compartments may for example be substantially cylindrical, which term includes shapes which have a circular, oval or oblate circular cross section across the longitudinal axis, and shapes which have parallel or tapering e.g. with side walls which taper conically over at least part of their extent. Such substantially cylindrical capsule compartments may be provided with connectable parts at one or both of their longitudinally disposed ends so that the assembled dosage form may also be overall of a substantially cylindrical shape.

Suitably, methacrylic acid copolymers (such as Eudragit E®, Eudragit E100® Eudragit® L and/or Eudragit® S), poly (meth)acrylate copolymers, such as Eudragit® 4135F, and ammonium methacrylate copolymers (such as Eudragit® RL and/or Eudragit® RS), are used for injection molding. The group of poly(meth)acrylate copolymers, such as Eudragit® 4135F are a preferred aspect of this invention.

Acrylic and/or methacrylic acid-based polymers which are soluble in intestinal fluids and which can be formed into capsules are for example disclosed in U.S. Pat. No. 5,705,189 (Roehm GmbH) the content of which is incorporated herein by reference in its entirety. These poly(meth)acrylate copolymers were extrudable and injection molded into capsule half's wherein the ratio of acrylic and/or methacrylic acid was generally 20% w/w or more off the copolymer (Examples 1-8). In these Examples, glycerol monostearate was added on a 3-5% wt base of the polymer as a mold-releasing agent.

A particular polymer disclosed in U.S. Pat. No. 5,705,189, emulsion E2 (column 6, line 10) being a copolymer of methacrylic acid, methyl methacrylate and methyl acrylate (suitably in a ratio of 10:25:65) has been found to be a preferred polymer for use in the present invention. This ratio of components is also known as Eudragit® 4135F, and is a solid product obtained from Eudragit® FS 30D, and as noted above is available from Rohm Pharma/Degussa, Darmstadt, Germany. However, it has been found that the unblended polymer alone is not suitable for injection molding, but must be blended in accordance with the teachings herein to produce suitable injection molded, non-distorted, unwarped capsule/sub-unit components for assembly into either single capsule or multicompartment dosage forms. For purposes herein, Eudragit® 4135F and various derivatives blends of similar ratios of components, i.e., copolymer blends of methacrylic acid, methyl methacrylate and methyl acrylate, such as 10 to 40% w/w methacrylic acid; 30-80% methyl acrylate; and 0 to 40% methyl methacrylate, including but not limited to those described in U.S. Pat. No. 5,705,189 as E1 and E3 emulsion polymers. Eudragit® 4135F has an average molecular weight of about 220,000.

For the polymer E 4135F, use of at least one lubricant and one dissolution modifying agent have been necessary to achieve quality, non-distortion molded components which readily release from the injection molds. As exemplified in U.S. Pat. No. 5,705,189 the polymers therein all have increased viscosity's relative to the blended compositions, as taught herein.

The polymer Eudragit 4135F™ dissolves only above pH 7, e.g. in the colon and so is suitable for formulation as a sustained release component. In contrast, the polymer Eudragit E100™ dissolves in acid as so is suitable for use as an immediate release component.

These and other pharmaceutically acceptable polymers are described in detail in the Handbook of Pharmaceutical excipients, published jointly by the American Pharmaceutical association and the Pharmaceutical society of Britain.

As noted, Eudragit® 4135F hydrates and begins to erode above a pH of 7.2. It has been found that there is a large intersubject variation of the intestinal luminal pH, and that it is difficult to achieve significant exposure to the capsule walls for the required pH in a large number of patients. Further, a shell wall thickness of 0.5 mm produces results which have a prolonged dissolution time for the unmodified polymer (>30 hrs). Consequently, to achieve a pulsatile release with this polymer in an injection molded shell, various excipients are needed in the formulation. Such agents include, but are not limited to, swelling agents, such as HPMC and super disintegrants; surfactants, such as SDS or the Pluronic groups; pore-forming/chanelling agents, such as lactose or PEG; additional polymers for co-blending such as HPMC, polyethylene oxide as POLYOX (Union Carbide), or hydroxypropylcellulose (HPC); and additional buffering agents for adjust of microclimate pH conditions.

A preferred co-blend with Eudragit® 4135F is the polymer HPC. One suitable brand is that marketed by Aqualon, a division of Hercules Incorporated, as Klucel®. Klucel® HPC is produced in various grades, as determined by their intended use. The Klucel® polymers of choice are Klucel® EF, Klucel® JH, Klucel® LF, and Klucel® GF, or combinations thereof. It is recognized that other Klucel polymers may be used in combination with a lower molecular weight polymer to produce a blended ingredient for use herein. Kluce® E has a viscosity in the range of 150-700 (a 200-600 mPas at a 10% concentration in aqueous solution at 25° C. for EF pharm; 300-600 mPas for EXF Pharm), and a molecular weight of about 80,000; JF has a viscosity of 150-400 mPas at 5% concentration in aqueous solution at 25° C., and a molecular weight of about 140,000, LF has a viscosity in the range of 75-150 mPas at a 5% concentration in aqueous solution at 25° C., and a molecular weight of about 95,000; GF has a viscosity in the range of 150-400 mPas at a 2% concentration in aqueous solution at 25° C., and a molecular weight of about 370,000; Kluce® M has a molecular weight of about 850,000 and a viscosity in the range of 4000-6500 mPas at a 2% concentration in aqueous solution at 25° C.; and Klucel® H as a molecular weight of about 1,150,00 and a viscosity in the range of 1500-3000 mPas at a 1% concentration in aqueous solution at 25° C.

Nippon Soda Co Ltd. also produces a commercial grade of hydroxypropyl cellulose under the trade name Nisso HPC, as Nisso HPC-L (viscosity of 6.0-10.0 mPas at a 2% concentration in aqueous solution at 20° C.), and HPC-M (viscosity of 150-400 mPas at a 2% concentration in aqueous solution at 20° C.).

For more details on Viscosity determinations in mPa's etc., of various grades of HPC see the Handbook of Pharmaceutical Excipients, 3rd Edition, (2000), pages 243-248 whose disclosure is incorporated by reference herein. For purposes herein, a grade of HPC may be referred to by an approximate molecular weight range, or in the alternative by its approximate viscosity range.

Further, a general reference may be made to either the individual polymer or a blend of hydroxypropylcellulose polymer may be made by a general classification of their molecular weights into groups, such as a low molecular weight hydroxypropylcellulose having a molecular weight equal to or >30,000 and <370,000; a medium molecular weight HPC has a molecular weight equal to or >370,000 and <850,000; and a high molecular weight HPC has a molecular weight equal to or >850,000 and <1,300,000. Suitably, the HPC polymer or the blend of HPC polymers is a low molecular weight of about equal to or >30,000 to about 370,000. In another embodiment the molecular weight range of the HPC polymer or the blend of HPC polymers is from about 50,000 to about 170,000, and suitably from about 80,000 to about 140,000. A blend can be achieved by combining in a number of variations the differing molecular weight hydroxypropyl cellulose polymers together. For use herein a limitation on the HPC polymer chosen is that it be suitable for injection molding. Therefore the polymer must be thermoplastic. Generally, the lowest molecular weight HPC's grades are not intrinsically thermoplastic. It is within the scope of this invention that if a blend of HPC polymers is used, it may comprises two polymers, or it may comprise more than two HPC polymers, and can be an amount w/w% any number of the HPC polymers to achieve the desired characteristics. While the experiments shown herein teach equal or near equal amounts of co-polymers, this is merely representative and not a limitation on the scope and breath of this invention. A blend of two polymers may be from slight greater than 0%, such as 0.1% w/w, having a ratio of 0.1:100 to 100:0.1, a blend of three polymers may be from 0.1:100:0.1 to 100:0.1:0.1 to 0.1:0.1:100, etc.

Addition of these polymers, which are thermoplastic polymers as noted above, provide for reduced sensitivity to welding conditions, improved tensile properties both pre and post hydration, and a more robust swelling of the polymer at pH of 1 to 6.

It has been determined that these co-blended polymers produces shells which hydrate and swell considerably more than the non-blended polymeric composition under a number of conditions. This produces a formulation which has significant improvements in dissolution reproducibility; the release of the capsule shells is influenced less by the weld settings; an enhanced hydration profile, which results in less structural integrity upon dissolution; and superior appearances, and tensile properties of the resulting shells.

The E4135 co-blended components have further been found to be stable after prolonged storage conditions.

The polymer polymethacrylate, Eudragit® 4135F is present in the formulation in an amount of about 20 to about 90% w/w, preferably from about 20 to about 40% w/w.

The amount of the hydroxypropylcellulose is from about 20 to about 70% w/w, preferably about 30 to about 60% w/w of the formulation. The individual amounts of each HPC, if more than one is present, may vary to achieve the total 20 to 70% overall w/w amount. In one embodiment of the present invention the compositions of Eudragit® 4135F comprise a blend of at least two hydroxypropylcellulose polymers of differing molecular weights.

While equal or near equal amounts may be used, to achieve the desired molecular weight blends, small amounts of higher molecular weight HPC's may be blended with small amounts of lower molecular weight HPC's, etc. Consequently, even smaller amounts, such as 10% w/w amount of and HPC polymer or blend may be suitable for use herein.

The co-blended formulations of E4135F with HPC have been found to produce an erodible, and a pH-independent formulation.

It is recognized that the polymeric compositions are first melted in a melt extrusion process, and may also contain additional additives or excipients to assist in melt flow, strength, brittleness, and other desired molding characteristics. These additional excipients include, but are not limited to, lubricants or glidants, plasticizers, absorption enhancers, additional surfactants, flavouring agents, and dyes, etc.

While the compositions herein may be molded in varying wall-thickness, it is preferably that capsules or components have a wall-thickness of about 0.3 to about 0.8 mm, suitably about 0.5 mm. However, dissolution performance will more appropriately tailor the wall thickness depending upon the release profiles desired. Increases in wall thickness may be necessary to reduce warping of the components, or modification of the additional excipients in addition to changes in wall thickness may also be necessary.

In addition to excipients or additives for the extrusion process, the polymeric compositions may include other substances to modify their properties and to adapt them to various applications. These may include those noted above, but in addition, may include, but are not limited to, surfactants, absorption enhancers, lubricants, plasticizers, dissolution modifying agents, processing aids, colouring agents, flavouring agents and sweetening agents.

Incorporation of a surfactant into the formulation may be necessary or desired to lower the viscosity and surface tension of the formulation blend, however, in higher amounts it may adversely effect the quality of the resulting dosage form. The surfactant selection may be guided by HLB values but it is not necessarily a useful criterion. While HLB values have been utilized herein, such as Tween® 80 (HLB=10), Pluronic F68 (HLB=28), and SDS (HLB>40), lower HLB value surfactants, such as Pluronic F92 and F127 may also be used. Pluronic, made by BASF, USA has a synonym of POLOXAMER. Pluronic F68, has a molecular weight of about 8,400. Pluronic F1127 has a molecular weight of about 12,600. Pluronics are block copolymers of ethylene oxide and propylene oxide and are also referred to as polyoxypropylene-polyoxyethylene block copolymers.

A surfactant may also be called an oligomeric surface modifier and includes, but is not limited to: Pluronics®; lecithin, Aerosol OT® (sodium dioctyl sulfosuccinate), sodium lauryl sulfate (also referred to as sodium dodecyl sulfate (SDS), Polyoxyl 40™ hydrogenated castor oil, polyoxyethylene sorbitan fatty acid esters, i.e., the polysorbates such as Tween®, such as Tween 20, 60 & 80, the sorbitan fatty acid esters, i.e., sorbitan monolaurate, monooleate, monopalmitate, monostearate, etc. such as Span® or Arlacel®, Emsorb®, Capmul®, or Sorbester®, Triton X-200, polyethylene glycol's, glyceryl monostearate, Vitamin E-TPGS® (d-alpha-tocopheryl polyethylene glycol 1000 succinate), sucrose fatty acid esters, such as sucrose stearate, sucrose oleate, sucrose palmitate, sucrose laurate, and sucrose acetate butyrate, etc.; and combinations and mixtures thereof. In one embodiment of the present invention, surfactants such as Vitamin E-TPGS®, sodium lauryl sulfate, sucrose fatty acid esters, lecithin, and the Pluronic groups, or a combination/mixture thereof, are used. In another embodiment of the present invention, surfactants such as sodium lauryl sulfate or a block copolymers of ethylene oxide and propylene oxide, or a combination or mixture thereof are used.

Suitably, the formulation may optionally contain from about 0 to about 10% w/w surfactant(s). Suitably, if SDS (Texapon K-12®) or a block copolymers of ethylene oxide and propylene oxide is used in the formulation, they are present in an amount less than 2% by weight, more preferably <1% w/w.

The polymeric carriers or oligomeric surface modifiers, if appropriately chosen, may themselves act as absorption enhancers. Suitable absorption enhancers for use herein, also include but are not limited to, chitosan, lecithin, lectins, sucrose fatty acid esters such as the those erived from stearic acid, oleic acid, palmitic acid, lauric acid, and Vitamin E-TPGS, and combinations or mixtures thereof. Suitably, these absorption enhancers are present in a range of about 0 to about 20% w/w.

Plasticizers may also be employed to assist in the melting characteristics of the composition. Exemplary of plasticizers that may be employed in this invention are triethyl citrate (TEC), triacetin, tributyl citrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, or castor oil; and combinations or mixtures thereof. The polymeric co-blended material will determine which plasticizer is suitable for use. For instance, triacetin is generally not preferred for use with Eudragit 4135F at levels of about 5%. Suitably, the plasticizer is present in an amount of about 0 to about 20% w/w. Preferably, the plasticizer may be present from about 0 about 5% w/w. In one embodiment of the present invention, the ability to form an injection molded shell of a Eudragit® 4135F formulation without the addition of a plasticizer such as those noted above may be achieved.

Dissolution modifying agents, or substances are those which assist in release modifications that alter the erosion and/or swelling characteristics of the shell. Many different classes of agents may be used, and are further described in more detail below, but include those classes such as the known disintegrants represented by "Explotab" (sodium starch glycollate), "Kollidon-CL", (cross-linked PVP), Kollidon VA 64 (copovidone) commercially available from BASF, Starch 1500; swelling solids or agents such as polyvinyl pyrrolidone (PVP, also know as Povidone, USP), manufactured by ISP-Plasdone or BASF-Kollidon, primarily grades with lower K values (K-15, K-25, but also K-30 to K-90), the cellulosic derivatives such as hydroxypropyl methyl cellulose (HPMC), wicking agents such as low molecular weight solutes, e.g. xylitol, mannitol, lactose, and starch; and inorganic salts such as sodium chloride (typically at levels of about 5 to about 10%).

Kollidan VA 64, or copovidone, is also known as copolyvidone, copovidonum, copovidone or copovidon, is the ratio of two monomers, vinylpyrrolidone and vinyl acetate.

More specifically, the class of agents known as swellable solids which may be used as dissolution modifying agents, include but is not limited to poly(ethylene)oxide, the cellulosic derivatives, such as ethyl cellulose and cellulose acetate phthalate; hydroxypropylcellulose (HPC), especially at lower molecular weights, e.g., KLUCEIL EF and LE grades, hydroxypropylmethylcellulose, and other hydroxyalkylcellulose derivatives. Suitably, the swellable solids used as dissolution modifying excipients are present in the range of about 5% to about 70%w/w. Other suitable dissolution modifying excipients include, but are not limited to the class of non-reducing sugars, such as xylitol, or mannitol, present in the range of about 2.5 to about 15% w/w. Also included are the class of water soluble fillers, such as lactose, and starch, suitably present in the range of about 5 to about 20%.

Another group of the dissolution modifying excipients referred to as disintegrants may be used, such as sodium starch glycolate, croscarmellose sodium NF (Aci-Di-Sol® produced by FMC), copovidone, and crospovidone (cross-linked polyvinyl pyrrolidone); and combinations or mixtures thereof. Suitably, the class of disintegrants are present in the range of about 10 to 40%, more preferably from about 20 to about 30% w/w. It is recognized that the one of more classes of dissolution modifying excipients may be used alone, or in combination as mixtures with each other, resulting in a total range of about 2.5 to about 70% w/w being present in the formulation. One such combination is croscarmellose sodium and sodium starch glycolate. Another is the combination of hydroxypropylcellulose and lactose.

Additional regents, generally classified as processing aids or strengthening agents, and may include such ingredients as talc. Suitably, the processing aids are present from about 0 to about 10% w/w.

The formulations may also entail mold processing agents, such as lubricants or glidants. These include but are not limited to, stearyl alcohol, stearic acid, glycerol monostearate (GMS), talc, magnesium stearate, silicon dioxide, amorphous silicic acid, fumed silica and lecithin; and combinations or mixtures thereof. These function primarily as flow promoters for the composition. A suitable grade of stearyl alcohol, is a commercial grade, such as Crodacol S95 (Croda Oleochemicals). The material chosen as a lubricant should also be suitable for milling. In one embodiment of the present invention is the lubricant is stearyl alcohol, or GMS. In another embodiment of the present invention the lubricant is stearyl alcohol.

Suitably, the amount of lubricant present in the formulation is from about 0 15 to about 30% w/w, more suitably from about 10 to about 25% w/w, and most suitably from about 10 to about 15% w/w. In a preferred embodiment for stearyl alcohol, it is present from about 10 to about 20%w/w, and more preferably from about 12 to about 15% w/w.

Stearyl alcohol has the advantage that it acts as a mold processing lubricant but causes no mold distortion, i.e. crumpling of the multidosage compartment shell when the hot soft shell is taken out of the mold, which might result from a lubricant which made the blend flow better. Suitably, the lubricants for use herein do not introduce any metal ion contamination, particularly if a natural product, such as lecithin is used.

Inclusion of a lubricant, such as stearyl alcohol, has been found to enhance flow. It is also found that higher proportions of stearyl alcohol increase the flowability so as to enable molding of thinner walls.

One embodiment of the present invention is the combination of a stearyl alcohol, a swellable solid, sodium starch glycollate and/or croscarmellose sodium; the polymer hydroxypropylcellulose or blends of HPC, a surfactant, and the polymer Eudragit® 4135F or a similar co-polymer blend. Suitably, if the surfactant is SDS it is present at 2% w/w or less, more preferably 1% or less, and less than <20% w/w swellable solids. Suitably, the sodium starch glycollate and/or croscarmellose sodium is present in about a 10% w/w amount.

The final products of this invention, i.e. the capsules, and or components or the sub-units may also additionally include materials in the polymer composition of which they are made to enhance the ease with which they can be welded together, e.g. opacifier materials such as carbon (e.g. 0.2-0.5%), iron oxides or titanium dioxide (e.g. 0.5-1.0%) which may help the polymer to absorb laser energy. Such opacifier materials are generally regarded as safe.

For example each of a plurality of sub units, e.g. of the capsule compartments, solid sub-units, or combinations thereof may comprise the same or different polymer(s). For example each of a plurality of sub units, e.g. of capsule compartments, solid sub-units, or combinations thereof may comprise the same or different drug substance. For example each sub-unit may contain the same drug substance but release the contents into the gastro-intestinal tract of the patient at a different rate, at different times after administration to the patient or at different places in the patient's gastro-intestinal system. Alternatively each sub-unit may contain a different drug substance, each of which may be released at the same or a different rate or time after administration or place in the patient's gastro-intestinal system.

For example two or more sub-units, e.g. two capsule compartments, may each contain different drug substances, and/or different drug substance formulations, and/or the same drug in different formulations, so that a combination of two or more drug substances or formulations may be administered to a patient.

The dosage form of this invention enables the assembly together of sub-units which differ in their drug content and/or drug content release characteristics to provide a dosage form tailored to specific administration requirements.

The dimensions and shape of each of the sub-units and hence of the overall assembled dosage form may be determined by the nature and quantity of the material to be contained therein and the intended mode of administration and intended recipients. For example a dosage form intended for oral administration may be of a shape and size similar to that of known capsules intended for oral administration.

The dosage form is particularly suitable for presentation as an oral dosage form containing one or more drug substances suitable for oral administration, and appears to be suitable for all types of such drug substance.

The drug substance(s) contained in any capsule compartment may be present in any suitable form, e.g. as a powder, granules, compact, microcapsules, gel, syrup or liquid provided that the capsule compartment wall material is sufficiently inert to the liquid content of the latter three forms. The contents of the compartments, e.g. drug substances, may be introduced into the compartments by standard methods such as those used conventionally for filling capsules, such as dosating pins or die filling.

The sub-units may differ from each other in their drug content release characteristics, and this may be achieved in various ways. For example one or more solid sub-units and/or capsule compartments may be substantially immediate release, i.e. releasing their drug contents substantially immediately upon ingestion or on reaching the stomach. This may for example be achieved by means of the matrix polymer or the capsule compartment wall dissolving, disintegrating or otherwise being breached to release the drug content substantially immediately. Generally, immediate-release sub-units are preferably provided by being capsule compartments.

For example one or more solid sub-units and/or capsule compartments may be sustained-release sub-units. Preferably these are solid sub-units, as a bulk matrix of polymer is likely to dissolve or disperse more slowly to release its drug content that a thin walled capsule.

For example one or more solid sub-units and/or capsule compartments may be pulsed-release sub-units for example releasing their drug content at a specific predetermined point in a patient's gastro-intestinal system. This may be achieved by the use of polymer materials which dissolve or disperse only at defined pH environments, such as the above mentioned Eudragit® polymers. For instance, E100 is acid labile.

For example in the above-described capsule compartment-linker-capsule compartment dosage form one capsule compartment may be effectively immediate release and the other may be sustained, delayed or pulsed release. To achieve this for example one capsule compartment may be made of polymer materials which cause the capsule compartment to release its drug content in the stomach or upper part of the digestive tract, and the linker (acting as a closure for the second compartment) and the second compartment itself may be made of materials e.g. the above described enteric polymers, which release their drug content only in the intestinal environment.

Determination of the time or location within the gastrointestinal tract at which a sub-unit releases its drug substance content may be achieved by for example the nature of the sub-unit material, e.g. a solid sub-unit matrix polymer or a capsule compartment wall material, or in the case of an end compartment which is closed by a closure, by the nature of the closure material. For example the wall of different, e.g. adjacent, compartments may be made of polymers which are different or which otherwise differ in their dissolution or disintegration characteristics so as to endow different compartments with different drug release characteristics. Similarly for example the polymer matrix material of different, e.g. adjacent, solid sub-units may be made of polymers which are different or which otherwise differ in their dissolution or disintegration characteristics so as to endow different solid sub-units with different drug release characteristics.

For example the matrix, wall or closure material may be a polymer which dissolves or disperses at stomach pH to release the drug substance in the stomach. Alternatively the wall material of different compartments may differ so that different compartments have different release characteristics.

For example a solid sub-unit or a capsule compartment may have respectively a matrix or a wall or a closure comprising an enteric polymer which dissolves or disperses at the pH of the small or large intestine to release the drug substance in the intestine. Suitable such polymers have been described above, for example, with reference to U.S. Pat. No. 5,705,189.

Additionally or alternatively the wall material may differ in thickness between compartments so that thicker walled compartments disrupt more slowly than thinner walled compartments.

Additionally or alternatively the compartment walls or the closure may have areas or points of weakness which preferentially dissolve and may thereby determine the time of onset and/or rate of release of the drug substance content. For example such points of weakness may comprise holes, e.g. small holes, e.g. laser-drilled holes in the compartment wall or the closure, these holes being closed and/or covered with a film of a polymer material that dissolves at a pre-determined point in the digestive tract, for example an enteric polymer material. For example such points of weakness may comprise thinned parts in a capsule compartment wall formed during the molding operation in which the capsule compartment is formed.

The sub-units may additionally or alternatively have surface or other constructional features that modify their drug release characteristics. For example solid sub-units may be provided with internal cavities or channels to create a large surface area. For example solid sub-units may be in the form of hollow cylinders, donuts, or toroids, which shapes are known to tend towards first-order dissolution or erosion in liquid media and correspondingly to tend toward first-order release of drug content dispersed therein.

Pharmaceutically acceptable agents, actives or drugs as used herein, is meant to include active agents having a pharmacological activity for use in a mammal, preferably a human. The pharmacological activity may be prophylactic or for treatment of a disease state.

As used herein the term's "active agent", "drug moiety" or "drug" are used interchangeably.

Water solubility of an active agent is defined by the United States Pharmacoepia. Therefore, active agents which meet the criteria of very soluble, freely soluble, soluble and sparingly soluble as defined therein are encompassed this invention.

Suitable drug substances can be selected from a variety of known classes of drugs including, but not limited to, analgesics, anti-inflammatory agents, anthelmintics, anti-arrhythmic agents, antibiotics (including penicillin's), anticoagulants, antidepressants, antidiabetic agents, antiepileptics, antihistamines, antihypertensive agents, antimuscarinic agents, antimycobactefial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, PDE IV inhibitors, NK3 inhibitors, CSBP/RK/p38 inhibitors, antipsychotics, vasodilators and xanthines.

Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference in its entirety. The drug substances are commercially available andlor can be prepared by techniques known in the art.

The polymeric blends can be preferably selected from known pharmaceutical polymers. The physico-chemical characteristics of these polymers, as well as the thickness of the ultimate injection molded component, will dictate the design of the dosage form, such as rapid dissolve, immediate release, delayed release, modified release such as sustained release, controlled release, or pulsatile release. etc.

The polymer blends are made by well-known methods for producing hot melt extrusions in which the selected ingredients are fed into a feed hopper of an extrusion machine. Suitable well known equipment is readily available for producing a hot melt extrusion of the blends herein.

For production of an early release capsule or component in a multidosage capsule, (such as in a 2 hour window), the polymer Eudragit® 4135F (Röhm), may be extruded into a thin walled component shell (such as those indicated herein), by blending with several excipients as noted herein. As will be seen by the experimental section, formulation with a lubricant, and a co-blend of hydroxypropyl cellulose has now been shown to produce a stable, injection molded component which can be reliably reproduced and injected from the mold with reduced, or no warpage of the shell.

In addition it has been found that use of a blend of hydroxypropylcellulose can provide for an unexpected reduction in necessary components of the formulation, thereby reducing cost, and mixing times.

Experiments with Klucel® HPC at various percentages, ranging from 30 to 70% have been formulated and tested for the variance in dissolution times. Formulations containing 30 to 60% Klucel® have been found to have similar dissolutions times (<2 hours) in both simulated gastric fluid and simulated intestinal fluids. Dissolutions times for formulations containing less than 30% Klucel® are longer and more variable indicating that an increased level of greater than 40% of Klucel® is necessary to provide reproducible release profiles.

To ensure a slower release, the pharmaceutical formulations include various hydrophilic excipients. Preferably, the hydrophilic excipient is one which does not melt at the extrusion temperature, e.g. the lactose, inorganic salts, HPC, HPMC, such as Pharmacoat 603 (an HPMC with a glass transition temperature of about 175° C.). In another embodiment copovidone has also been found to be a useful ingredient with Eudragit® F4135, along with HPMC, as well as other cellulosics or swellable agents. As noted, these swellable solids are available commercially in a number of grades by molecular weight, for examples 95K, or 80K grades of HPC. A change in the molecular weight of HPC, for instance, should retain the ability to hydrate the shell, but the hydration rate may be slower, i.e. the rate of expansion will be reduced. Hence, a longer dissolution time of the shell and release of the components therein may result. Experiments with Klucel® HPC at various percentages, and with differing molecular weights have been formulated and tested for the variance in dissolution times. Formulations containing 40 to 70% Klucel®

EXAMPLES

The invention will now be described by reference to the following examples, which are merely illustrative and are not to be construed as a limitation of the scope of the present invention. All temperatures are given in degrees centigrade; all solvents are highest available purity unless otherwise indicated. While it is also recognized that incomplete mold filings, or cracking of the capsule shells is not ideal for a finished commerical product, it is indicative of formulations which are moldable and injectable within the context of this invention.

Example 1

Manufacture of multicomponent pharmaceutical dosage forms with pharmaceutically acceptable polymeric compositions are described herein. Using the general process conditions described in U.S. Ser. No. 10/060,849 or WO 02/060384, published Aug. 8, 2002, these formulations may be used to mold various multicomponent capsules and appropriate subunits. U.S. Ser. No. 10/060,849 describes the extrusion and injection molding conditions for the component parts such as use of a 16 or 19 mm APV extruder and a MCP machine.

Formulations containing Eudragit® 4135F and hydroxypropylcellulose (various molecular weight combinations of Klucel®) were extruded, pelletised and then injection moulded.

| Component | Ex. 1 | Ex. 2 % w/w | Ex. 3 |
|---|---|---|---|
| Eudragit ® 4135F | 24.0 | 24.0 | 24.0 |
| Stearyl alcohol | 12.0 | 12.0 | 12.0 |
| Klucel ® EF | 30.0 | 30.0 | 0.0 |
| Klucel ® JF | 30.0 | 0.0 | 30.0 |
| Klucel ® GF | 0.0 | 30.0 | 30.0 |
| Explotab | 2.0 | 2.0 | 2.0 |
| SDS | 1.0 | 1.0 | 1.0 |
| Pluronic F68 | 1.0 | 1.0 | 1.0 |
|  | 100 | 100 | 100 |

The shells, manufactured using the 0.5 mm wall section mould tool, were found to be extremely flexible, a quality attributed to the presence of Klucel® in the blend.

Formulations of Example 1 and Example 2 were tested using the USP3 dissolution apparatus. The shells were ultrasonically welded to a Eudragit® 4135F/10% Pharmacoat/12% Stearyl alcohol linker using a maximum weld strength. All but one sample released at approximately 1.5 hrs. There did not appear to be a significant difference in release time between the two formulations.

Example 4

| Formulation | |
|---|---|
| | % w/w |
| Eudragit ® 4135F | 24.00 |
| Klucel ® LF | 30.00 |
| Klucel ® JF | 30.00 |
| Stearyl alcohol | 12.00 |
| Explotab | 2.00 |
| Texapon K-12 | 1.00 |
| Pluronic F68 | 1.00 |

The formulation was extruded and pelletised, however on injection moulding at 175° C. incomplete filling of the mould occurred.

Example 5

| Formulation | |
|---|---|
| | % w/w |
| Eudragit ® 4135F | 24.00 |
| Klucel ® LF | 30.00 |
| Klucel ® GF | 30.00 |
| Stearyl alcohol | 12.00 |
| Explotab | 2.00 |
| Texapon K-12 | 1.00 |
| Pluronic F68 | 1.00 |

The formulation was extruded and pelletised, however on injection moulding at 175° C. incomplete filling of the mould occurred.

Example 6

| Formulation | |
|---|---|
| | % w/w |
| Eudragit ® 4135F | 24.00 |
| Klucel ® JF | 30.00 |
| Klucel ® GF | 30.00 |
| Stearyl alcohol | 12.00 |
| Explotab | 2.00 |
| Texapon K-12 | 1.00 |
| Pluronic F68 | 1.00 |

The formulation was extruded and pelletised, however on injection moulding with a 0.5 mm wall section at 175° C. incomplete filling of the mould occurred.

Example 7

| Formulation | |
|---|---|
| | % w/w |
| Eudragit ® 4135F | 24.00 |
| Klucel ® EF | 32.00 |
| Klucel ® JF | 32.00 |
| Stearyl alcohol | 12.00 |

The formulation was extruded, pelletised and injection molded with 0.3 mm and 0.5 mm wall sections at 178° C., shells were produced satisfactorily.

The 0.5 mm shells produced under this Example were tested using USP3 dissolution apparatus at a dip speed of 5 dips per minute (dpm). The samples all release between 45-60 minutes in a USP3, and after 2 hours all the shells have become completely detached from the linker (Eudragit® 4135F/10% pharmacoat/12% stearyl alcohol). The release mechanism appears to be swelling of the matrix over a period of time, detachment appears to be largely independent of the weld conditions used to seal the units.

Example 8

| Formulation | |
|---|---|
| | % w/w |
| Eudragit ® 4135F | 29.00 |
| Klucel ® EF | 25.00 |
| Klucel ® JF | 30.00 |
| Stearyl alcohol | 12.00 |
| Explotab | 2.00 |
| Texapon K-12 | 1.00 |
| Pluronic F68 | 1.00 |

The formulation was extruded, pelletised and then injection molded with 0.3 mm and 0.5 mm wall sections at 185° C. The 0.5 mm shells were satisfactory, however small cracks were apparent in some of the 0.3 mm shells.

Example 9

| Formulation | |
|---|---|
| | % w/w |
| Eudragit ® 4135F | 10.00 |
| Klucel ® EF | 70.00 |
| Stearyl alcohol | 12.00 |
| Explotab | 5.00 |
| Texapon K-12 | 1.00 |
| Pluronic F68 | 2.00 |

The formulation was extruded, pelletised and injection molded into 0.3 mm and 0.5 mm wall sections shells at 185° C. Occasional gate blockage occurred during production of the 0.3 mm shells.

Example 10

| Formulation | |
|---|---|
| | % w/w |
| Eudragit ® 4135F | 10.00 |
| Klucel ® LF | 70.00 |
| Stearyl alcohol | 12.00 |
| Explotab | 5.00 |
| Texapon K-12 | 1.00 |
| Pluronic F68 | 2.00 |

The formulation was extruded, pelletised and then injection molded with a 0.5 mm wall section at 185° C.; attempts to produce shells with a 0.3 mm wall section were abandoned as repetitive gate blockage occurred.

Example 11

| Formulation | |
|---|---|
| | % w/w |
| Eudragit ® 4135F | 15.00 |
| Klucel ® EF | 55.00 |
| Stearyl alcohol | 12.00 |
| Explotab | 2.00 |
| Texapon K-12 | 1.00 |
| Lactose | 15.00 |

The formulation was extruded at 1 kg/hr with a die temp. of 110° C. and a 200 rpm screw speed. These conditions produced a motor torque of 38% and a die pressure of 4 bar. The injection moulded 0.5 mm wall section shells contained small cracks in about 50% of the samples. As an alternative example, 0.3 mm shells were also molded at 165° C. and in this instance 100% shells were found to contain cracks; additionally at a temperature of 170° C. a yellow colouration was found to occur, perhaps due to decomposition of lactose.

Example 12

| Formulation | |
|---|---|
| | % w/w |
| Eudragit ® 4135F | 15.00 |
| Klucel ® EF | 55.00 |
| Stearyl alcohol | 12.00 |
| Explotab | 2.00 |
| Texapon K-12 | 1.00 |
| Mannitol | 15.00 |

The formulation was extruded at 1 kg/hr, with a die temp. of 110° C. and a screw speed of 200 rpm resulting in a motor torque of 38%, and a die pressure of 3 bar. The injection moulded 0.5 mm wall section shells exhibited small cracks in about 50% of the sample (moulded at 170° C.). In an alternative experiment using this formulation 0.3 mm shells were also injection molded, 100% of shells were found to contain cracks(moulded at 180° C.)

Example 13

| Formulation | |
|---|---|
| | % w/w |
| Eudragit ® 4135F | 15.00 |
| Klucel ® EF | 55.00 |
| Stearyl alcohol | 12.00 |
| Explotab | 2.00 |
| Texapon K-12 | 1.00 |
| Mannitol | 15.00 |

The formulation was extruded at 1 kg/hr with a die temp. of 110° C. and a 200 rpm screw speed resulting in a motor torque of 43% and a die pressure of 3 bar. The 0.5 mm wall section shells injection moulded at 165° C. were satisfactory, however the 0.3 mm shells injection moulded at 175° C. contained small cracks in approximately 50% of the sample.

Example 14

Using shells produced in accordance with Example 7, the 0.3 mm shells were film coated with 5%, 10%, and 15% Eudragit® L30D-55 as an enteric coat in an Aeromatic Aerocoater. The dissolution results indicate that the 15% enteric coat provides the necessary delay in release along with the most reproducible release times. The release was determined to be about 2 hours +/−20 min for 11 of the 12 samples tested.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. An extruded and injection-molded multi-component pharmaceutical dosage form comprising a plurality of sub-units comprising:
a capsule shell providing pulsatile release of a drug substance contained within the shell, wherein the shell comprises a substantially pH-independent pharmaceutical composition comprising:
i) a copolymer of methyl acrylate, methyl methacrylate and methacrylic acid, with a molecular weight of about 220,000 and a ratio of free carboxyl groups to ester groups of 1:10 present in an amount of about 15 to about 50% w/w,
ii) at least two hydroxypropylcellulose polymers, present in an amount of about 20% to about 70% w/w, wherein one of the hydroxypropylcellulose polymers is a hydroxypropylcellulose polymer with an average molecular weight of 80,000 and the second hydroxypropylcellulose polymer is selected from a group consisting of a hydroxypropylcellulose polymer with an average molecular weight of 140,000 and a hydroxypropylcellulose polymer with an average molecular weight of 370,000;
iii) a lubricant present in an amount of about 10% to about 25% w/w;
iv) at least one dissolution modifying excipient selected from a disintegrant, a swellable solid, a non-reducing sugar, a water soluble filler, a wicking agent, or an inorganic salt, in combination or mixture thereof, present in an amount of about 2.5% to about 70% w/w;
v) a surfactant present in an amount of about 0 to about 10%, and
vi) a plasticizer present in an amount of about 0 to about 10% w/w and/or a processing agent present in an amount of 0 to about 10% w/w; and
a solid sub-unit comprising a pharmaceutical polymeric composition soluble, dispersible or disintegrable in a patient's gastro-intestinal environment for release of a second drug substance contained in the solid sub-unit, and
wherein at least prior to administration to a patient, the capsule shell is filled with the drug substance, and the plurality of sub-units are assembled into the dosage form.

2. The multi-component pharmaceutical dosage form according to claim 1, wherein the capsule shell has a wall thickness ranging from about 0.3 to about 0.8 mm.

3. The multi-component pharmaceutical dosage form according to claim 1, wherein the capsule shell and the solid sub-unit have different dissolution or disintegration characteristics in the patient's gastro-intestinal environment.

4. The multi-component pharmaceutical dosage form according to claim 1, wherein the capsule shell comprises a hydroxypropylcellulose polymer having a molecular weight of about 80,000, and a hydroxypropylcellulose polymer having a molecular weight of about 140,000 and wherein each polymer is present in an amount of about 30 to about 32% w/w.

5. The multi-component pharmaceutical dosage form according to claim 1, wherein capsule shell comprises a hydroxypropylcellulose having a molecular weight of about 80,000 and a hydroxypropylcellulose polymer having a molecular weight of about 370,000, and wherein each polymer is present in an amount of about 30 to about 32% w/w.

6. The multi-component pharmaceutical dosage form according to claim 1, wherein the lubricant is selected from the group consisting of stearyl alcohol, glycerol monostearate (GMS), talc, magnesium stearate, silicon dioxide, amorphous silicic acid, fumed silica, and mixtures thereof.

7. The multi-component pharmaceutical dosage form according to claim 6 wherein the lubricant is stearyl alcohol.

8. The multi-component pharmaceutical dosage form according to claim 7 wherein the stearyl alcohol is present in an amount of about 10 to about 15% w/w.

9. The multi-component pharmaceutical dosage form according to claim 1 wherein the at least one dissolution modifying excipient is selected from the group consisting of a disintegrant and a swellable solid, the non-reducing sugar is selected from the group consisting of xylitol and mannitol, the water soluble filler is selected from the group consisting of lactose and starch, the inorganic salt is sodium chloride, and mixtures thereof.

10. The multi-component pharmaceutical dosage form according to claim 9 wherein the disintegrant is selected from a group consisting of sodium starch glycollate, croscarmellose sodium, crospovidone, copovidone, and mixtures thereof.

11. The multi-component pharmaceutical dosage form according to claim 10 wherein the disintegrant is present in an amount of about 10 to about 40% w/w.

12. The multi-component pharmaceutical dosage form according to claim 10 wherein the disintegrant is present in an amount of about 20 to about 30% w/w.

13. The multi-component pharmaceutical dosage form according to claim 1 wherein the plasticizer is selected from a group consisting of triethyl citrate (TEC), tributyl citrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, castor oil and mixtures thereof.

14. The multi-component pharmaceutical dosage form according to claim 1 wherein the processing agent is talc present in an amount of about 1 to about 5% w/w.

15. The multi-component pharmaceutical dosage form according to claim 1 wherein the solid sub-unit composition further comprises an absorption enhancer.

16. The multi-component pharmaceutical dosage form according to claim 15 wherein the absorption enhancer is selected from the group consisting of chitosan, lecithin, lectin, a sucrose fatty acid ester, Vitamin E-TPGS and mixtures thereof.

17. The multi-component pharmaceutical dosage form according to claim 1 wherein the copolymer is present in an amount of about 15 to about 30% w/w.

18. The multi-component pharmaceutical dosage form according to claim 1, wherein the surfactant is present in an amount of less than about 5% w/w.

19. The multi-component pharmaceutical dosage form according to claim 18 wherein the surfactant is selected from the group consisting of sodium dodecyl sulphate and a block copolymer of ethylene oxide and propylene oxide.

20. The multi-component pharmaceutical dosage form according to claim 19 wherein the sodium dodecyl sulphate is present in an amount of less than about 2% w/w.

21. The multi-component pharmaceutical dosage form according to claim 1 wherein the lubricant is stearyl alcohol, and the at least one dissolution modifying excipient is a disintegrant selected from the group consisting of sodium starch glycollate, croscarmellose sodium, and mixtures thereof.

22. The multi-component pharmaceutical dosage form according to claim 1 wherein the surfactant is sodium dodecyl sulphate, present in an amount of less than about 2% w/w, and the swellable solid is present in an amount of less than about 20% w/w.

23. The multi-component pharmaceutical dosage form according to claim 21 wherein the sodium starch glycollate and/or croscarmellose sodium are present in an amount of about 10% w/w.

24. The multi-component pharmaceutical dosage form according to claim 1, wherein the copolymer is present in an amount of about 15 to about 25% w/w.

25. The multi-component pharmaceutical dosage form according to claim 1 wherein the pharmaceutical composition is selected from the group consisting of:

Copolymer 24%, Stearyl alcohol 12%, hydroxypropylcellulose polymer having a molecular weight of 80,000 30%, hydroxypropylcellulose polymer having a molecular weight of 140,000 30%, sodium starch glycollate 2%, sodium dodecyl sulfate 1%, and polyoxypropylene-polyoxyethylene block copolymers 1%;

Copolymer 24%, Stearyl alcohol 12%, hydroxypropylcellulose polymer having a molecular weight of 80,000 30%, hydroxypropylcellulose polymer having a molecular weight of 370,000 30%, sodium starch glycollate 2%, sodium dodecyl sulfate 1%, and polyoxypropylene-polyoxyethylene block copolymers 1%;

Copolymer 24%, Stearyl alcohol 12%, hydroxypropylcellulose polymer having a molecular weight of 140,000 30%, hydroxypropylcellulose polymer having a molecular weight of 370,000 30%, sodium starch glycollate 2%, sodium dodecyl sulfate 1%, and polyoxypropylene-polyoxyethylene block copolymers 1%;

Copolymer 24%, Stearyl alcohol 12%, hydroxypropylcellulose polymer having a molecular weight of 80,000 32%, hydroxypropylcellulose polymer having a molecular weight of 140,000 32%;

Copolymer 29%, Stearyl alcohol 12%, hydroxypropylcellulose polymer having a molecular weight of 80,000 25%, hydroxypropylcellulose polymer having a molecular weight of 140,000 30%, sodium starch glycollate 2%, sodium dodecyl sulfate 1%, and polyoxypropylene-polyoxyethylene block copolymers 1%; and Copolymer 21%, Stearyl alcohol 12%, hydroxypropylcellulose polymer having a molecular weight of 80,000 32%, hydroxypropylcellulose polymer having a molecular weight of 140,000 32%, sodium starch glycollate 2%, and polyoxypropylene-polyoxyethylene block copolymers 1%.

26. The multi-component pharmaceutical dosage form according to claim 1, wherein the plurality of sub-units contain the same drug substance.

* * * * *